US010526394B2

(12) United States Patent
Listek et al.

(10) Patent No.: US 10,526,394 B2
(45) Date of Patent: Jan. 7, 2020

(54) BIOMOLECULE-RELEASING CELL AND SELECTION THEREOF BY MEANS OF A SURFACE PROTEIN

(71) Applicant: NEW/ERA/MABS/GMBH, Potsdam (DE)

(72) Inventors: Martin Listek, Berlin (DE); Katja Hanack, Berlin (DE); Burkhard Micheel, Gerswalde (DE)

(73) Assignee: NEW / ERA / MABS GMBH, Potsdam (DE)

( * ) Notice: Subject to any disclaimer, the term of this patent is extended or adjusted under 35 U.S.C. 154(b) by 386 days.

(21) Appl. No.: 15/305,162

(22) PCT Filed: Apr. 20, 2014

(86) PCT No.: PCT/DE2014/000205
§ 371 (c)(1),
(2) Date: Oct. 19, 2016

(87) PCT Pub. No.: WO2015/161835
PCT Pub. Date: Oct. 29, 2015

(65) Prior Publication Data
US 2017/0044235 A1 Feb. 16, 2017

(51) Int. Cl.
*C07K 14/71* (2006.01)
*G01N 33/569* (2006.01)

(52) U.S. Cl.
CPC ....... *C07K 14/71* (2013.01); *G01N 33/56966* (2013.01); *C07K 2319/02* (2013.01);
(Continued)

(58) Field of Classification Search
CPC .......... C07K 1/14; C07K 14/71; C07K 16/00; C07K 2319/02; C07K 2319/03;
(Continued)

(56) References Cited

U.S. PATENT DOCUMENTS

| | | | | |
|---|---|---|---|---|
| 2006/0073095 A1 | 4/2006 | Kessler | | |
| 2010/0197009 A1* | 8/2010 | Lang | C07K 16/44 | 435/346 |
| 2014/0011213 A1* | 1/2014 | Helman | C12N 15/85 | 435/7.21 |

FOREIGN PATENT DOCUMENTS

| | | |
|---|---|---|
| EP | 0667896 B1 | 4/2003 |
| EP | 1141271 B1 | 4/2005 |

(Continued)

OTHER PUBLICATIONS

Listek M. et al., "Insertion of artificial cell surface receptors for antigen-specific labelling of hybridoma cells" Immunology, (2012) vol. 137, No. Suppl. 1, p. 185, 651, XP002734086, abstract.

(Continued)

*Primary Examiner* — Gailene Gabel
(74) *Attorney, Agent, or Firm* — Troutman Sanders LLP

(57) ABSTRACT

The invention relates, firstly, to a biomolecule-releasing cell characterised by a surface protein with an extracellularly exposed ligation peptide sequence for enzymatic conjugation of an adapter ligand, said adapter ligand being suitable for the indirect or direct coupling of a molecular catcher structure which has at least one specific binding site for the released biomolecules and which is at a distance from the specific binding site, secondly, to a method for selecting such a cell, and thirdly, to a means for this method comprising the surface protein that is characterised by an extracellularly exposable ligation peptide sequence for enzymatic conjugation of an adapter ligand, a nucleic acid coding for the surface protein, an expression vector for the nucleic acid, and a cell containing the expression vector.

9 Claims, 2 Drawing Sheets

Specification includes a Sequence Listing.

(52) U.S. Cl.
CPC ...... *C07K 2319/03* (2013.01); *C07K 2319/22* (2013.01); *C07K 2319/32* (2013.01); *C07K 2319/42* (2013.01)

(58) Field of Classification Search
CPC ............ C07K 2319/22; C07K 2319/32; C07K 2319/42; G01N 33/569; G01N 33/56966; C12N 5/07; C12N 5/0783
See application file for complete search history.

(56) References Cited

FOREIGN PATENT DOCUMENTS

| | | | |
|---|---|---|---|
| EP | 2272860 | A1 | 1/2011 |
| WO | 199409117 | A1 | 4/1994 |
| WO | 200042176 | A1 | 7/2000 |
| WO | 2003012449 | A2 | 2/2003 |
| WO | 2009010474 | A1 | 1/2009 |
| WO | 2012085911 | A1 | 6/2012 |
| WO | 2012164320 | A1 | 12/2012 |

OTHER PUBLICATIONS

Beckett D. et al., "A minimal peptide synthetase-catalyzied biotinylation" Protein Science, (1999) vol. 8, No. 4, pp. 921-929, XP002971557, ISSN: 0961-8368, abstract.
International Search Report dated Jan. 27, 2015 in connection with PCT/DE2014/000205.
Written Opinion dated Jan. 27, 2015 in connection with PCT/DE2014/000205.
International Preliminary Report on Patentability dated Oct. 25, 2016 in connection with PCT/DE2014/000205.

* cited by examiner

GTAT MRPSGTAGAALLALLAALCPASRA LEEGSSKLGSSG YPYDVPDYA GAQPARSGG
16→ 17→ 18→ 19→ 20→

GLNDIFEAQKIEWHE GAPATGSSG LEEKKVCQGTSNKLTQLGTFEDHFLSLQRMFNNCE
21→ 22→ 23→

VVLGNLEITYVQRNYDLSFLKTIQEVAGYALIALNTVERIPLENLQIIRGNMYYENSYALAVLSNY

DANKTGLKELPMRNLQEILHGAVRFSNNPALCNVESIQWRDIVSSDFLSNMSMDFQNHLGSC

QKCDPSCPNGSCWGAGEENCQRLTKIICAQQCSGRCRGKSPSDCCHNQCAAGCTGPRESD

CLVCRKFRDEATCKDTCPPLMLYNPTTYQMDVNPEGKYSFGATCVKKCPRNYVVTDHGSC

VRACGADSYEMEEDGVRKCKKCEGPCRKVCNGIGIGEFKDSLSINATNIKHFKNCTSISGDL

HILPVAFRGDSFTHTPPLDPQELDILKTVKEITGFLLIQAWPENRTDLHAFENLEIIRGRTKQH

GQFSLAVVSLNITSLGLRSLKEISDGDVIISGNKNLCYANTINWKKLFGTSGQKTKIISNRGEN

SCKATGQVCHALCSPEGCWGPEPRDCVSCRNVSRGRECVDKCNLLEGEPREFVENSECI

QCHPECLPQAMNITCTGRGPDNCIQCAHYIDGPHCVKTCPAGVMGENNTLVWKYADAGHV

CHLCHPNCTYGCTGPGLEGCPTNGPKIPS IATGMVGALLLLLVVALGIGLFM RRRHIVR-AA
24→ 25→

SEQUENCE LISTING

```
<160> NUMBER OF SEQ ID NOS: 14

<210> SEQ ID NO 1
<211> LENGTH: 24
<212> TYPE: PRT
<213> ORGANISM: Artificial Sequence
<220> FEATURE:
<223> OTHER INFORMATION: Homo sapiens

<400> SEQUENCE: 1

Met Arg Pro Ser Gly Thr Ala Gly Ala Ala Leu Leu Ala Leu Leu Ala
1               5                   10                  15

Ala Leu Cys Pro Ala Ser Arg Ala
            20


<210> SEQ ID NO 2
<211> LENGTH: 15
<212> TYPE: PRT
<213> ORGANISM: Artificial Sequence
<220> FEATURE:
<223> OTHER INFORMATION: Biotin acceptor peptide sequence

<400> SEQUENCE: 2
```

-continued

Gly Leu Asn Asp Ile Phe Glu Ala Gln Lys Ile Glu Trp His Glu
1 5 10 15

<210> SEQ ID NO 3
<211> LENGTH: 23
<212> TYPE: PRT
<213> ORGANISM: Artificial Sequence
<220> FEATURE:
<223> OTHER INFORMATION: Homo sapiens

<400> SEQUENCE: 3

Ile Ala Thr Gly Met Val Gly Ala Leu Leu Leu Leu Leu Val Val Ala
1 5 10 15

Leu Gly Ile Gly Leu Phe Met
20

<210> SEQ ID NO 4
<211> LENGTH: 630
<212> TYPE: PRT
<213> ORGANISM: Artificial Sequence
<220> FEATURE:
<223> OTHER INFORMATION: Homo sapiens

<400> SEQUENCE: 4

Gly Ala Pro Ala Thr Gly Ser Ser Gly Leu Glu Glu Lys Lys Val Cys
1 5 10 15

Gln Gly Thr Ser Asn Lys Leu Thr Gln Leu Gly Thr Phe Glu Asp His
20 25 30

Phe Leu Ser Leu Gln Arg Met Phe Asn Asn Cys Glu Val Val Leu Gly
35 40 45

Asn Leu Glu Ile Thr Tyr Val Gln Arg Asn Tyr Asp Leu Ser Phe Leu
50 55 60

Lys Thr Ile Gln Glu Val Ala Gly Tyr Ala Leu Ile Ala Leu Asn Thr
65 70 75 80

Val Glu Arg Ile Pro Leu Glu Asn Leu Gln Ile Ile Arg Gly Asn Met
85 90 95

Tyr Tyr Glu Asn Ser Tyr Ala Leu Ala Val Leu Ser Asn Tyr Asp Ala
100 105 110

Asn Lys Thr Gly Leu Lys Glu Leu Pro Met Arg Asn Leu Gln Glu Ile
115 120 125

Leu His Gly Ala Val Arg Phe Ser Asn Asn Pro Ala Leu Cys Asn Val
130 135 140

Glu Ser Ile Gln Trp Arg Asp Ile Val Ser Ser Asp Phe Leu Ser Asn
145 150 155 160

Met Ser Met Asp Phe Gln Asn His Leu Gly Ser Cys Gln Lys Cys Asp
165 170 175

Pro Ser Cys Pro Asn Gly Ser Cys Trp Gly Ala Gly Glu Glu Asn Cys
180 185 190

Gln Arg Leu Thr Lys Ile Ile Cys Ala Gln Gln Cys Ser Gly Arg Cys
195 200 205

Arg Gly Lys Ser Pro Ser Asp Cys Cys His Asn Gln Cys Ala Ala Gly
210 215 220

Cys Thr Gly Pro Arg Glu Ser Asp Cys Leu Val Cys Arg Lys Phe Arg
225 230 235 240

Asp Glu Ala Thr Cys Lys Asp Thr Cys Pro Pro Leu Met Leu Tyr Asn
245 250 255

Pro Thr Thr Tyr Gln Met Asp Val Asn Pro Glu Gly Lys Tyr Ser Phe

-continued

```
            260                 265                 270

Gly Ala Thr Cys Val Lys Lys Cys Pro Arg Asn Tyr Val Val Thr Asp
        275                 280                 285

His Gly Ser Cys Val Arg Ala Cys Gly Ala Asp Ser Tyr Glu Met Glu
    290                 295                 300

Glu Asp Gly Val Arg Lys Cys Lys Lys Cys Glu Gly Pro Cys Arg Lys
305                 310                 315                 320

Val Cys Asn Gly Ile Gly Ile Gly Glu Phe Lys Asp Ser Leu Ser Ile
                325                 330                 335

Asn Ala Thr Asn Ile Lys His Phe Lys Asn Cys Thr Ser Ile Ser Gly
            340                 345                 350

Asp Leu His Ile Leu Pro Val Ala Phe Arg Gly Asp Ser Phe Thr His
        355                 360                 365

Thr Pro Pro Leu Asp Pro Gln Glu Leu Asp Ile Leu Lys Thr Val Lys
    370                 375                 380

Glu Ile Thr Gly Phe Leu Leu Ile Gln Ala Trp Pro Glu Asn Arg Thr
385                 390                 395                 400

Asp Leu His Ala Phe Glu Asn Leu Glu Ile Ile Arg Gly Arg Thr Lys
                405                 410                 415

Gln His Gly Gln Phe Ser Leu Ala Val Val Ser Leu Asn Ile Thr Ser
            420                 425                 430

Leu Gly Leu Arg Ser Leu Lys Glu Ile Ser Asp Gly Asp Val Ile Ile
        435                 440                 445

Ser Gly Asn Lys Asn Leu Cys Tyr Ala Asn Thr Ile Asn Trp Lys Lys
    450                 455                 460

Leu Phe Gly Thr Ser Gly Gln Lys Thr Lys Ile Ile Ser Asn Arg Gly
465                 470                 475                 480

Glu Asn Ser Cys Lys Ala Thr Gly Gln Val Cys His Ala Leu Cys Ser
                485                 490                 495

Pro Glu Gly Cys Trp Gly Pro Glu Pro Arg Asp Cys Val Ser Cys Arg
            500                 505                 510

Asn Val Ser Arg Gly Arg Glu Cys Val Asp Lys Cys Asn Leu Leu Glu
        515                 520                 525

Gly Glu Pro Arg Glu Phe Val Glu Asn Ser Glu Cys Ile Gln Cys His
    530                 535                 540

Pro Glu Cys Leu Pro Gln Ala Met Asn Ile Thr Cys Thr Gly Arg Gly
545                 550                 555                 560

Pro Asp Asn Cys Ile Gln Cys Ala His Tyr Ile Asp Gly Pro His Cys
                565                 570                 575

Val Lys Thr Cys Pro Ala Gly Val Met Gly Glu Asn Asn Thr Leu Val
            580                 585                 590

Trp Lys Tyr Ala Asp Ala Gly His Val Cys His Leu Cys His Pro Asn
        595                 600                 605

Cys Thr Tyr Gly Cys Thr Gly Pro Gly Leu Glu Gly Cys Pro Thr Asn
    610                 615                 620

Gly Pro Lys Ile Pro Ser
625                 630
```

```
<210> SEQ ID NO 5
<211> LENGTH: 9
<212> TYPE: PRT
<213> ORGANISM: Artificial Sequence
<220> FEATURE:
<223> OTHER INFORMATION: Haemagglutinin A epitope
```

<400> SEQUENCE: 5

Tyr Pro Tyr Asp Val Pro Asp Tyr Ala
1 5

<210> SEQ ID NO 6
<211> LENGTH: 705
<212> TYPE: PRT
<213> ORGANISM: Artificial Sequence
<220> FEATURE:
<223> OTHER INFORMATION: Homo sapiens

<400> SEQUENCE: 6

Leu Glu Glu Gly Ser Ser Lys Leu Gly Ser Ser Gly Tyr Pro Tyr Asp
1 5 10 15

Val Pro Asp Tyr Ala Gly Ala Gln Pro Ala Arg Ser Gly Gly Gly Leu
20 25 30

Asn Asp Ile Phe Glu Ala Gln Lys Ile Glu Trp His Glu Gly Ala Pro
35 40 45

Ala Thr Gly Ser Ser Gly Leu Glu Glu Lys Lys Val Cys Gln Gly Thr
50 55 60

Ser Asn Lys Leu Thr Gln Leu Gly Thr Phe Glu Asp His Phe Leu Ser
65 70 75 80

Leu Gln Arg Met Phe Asn Asn Cys Glu Val Val Leu Gly Asn Leu Glu
85 90 95

Ile Thr Tyr Val Gln Arg Asn Tyr Asp Leu Ser Phe Leu Lys Thr Ile
100 105 110

Gln Glu Val Ala Gly Tyr Ala Leu Ile Ala Leu Asn Thr Val Glu Arg
115 120 125

Ile Pro Leu Glu Asn Leu Gln Ile Ile Arg Gly Asn Met Tyr Tyr Glu
130 135 140

Asn Ser Tyr Ala Leu Ala Val Leu Ser Asn Tyr Asp Ala Asn Lys Thr
145 150 155 160

Gly Leu Lys Glu Leu Pro Met Arg Asn Leu Gln Glu Ile Leu His Gly
165 170 175

Ala Val Arg Phe Ser Asn Asn Pro Ala Leu Cys Asn Val Glu Ser Ile
180 185 190

Gln Trp Arg Asp Ile Val Ser Ser Asp Phe Leu Ser Asn Met Ser Met
195 200 205

Asp Phe Gln Asn His Leu Gly Ser Cys Gln Lys Cys Asp Pro Ser Cys
210 215 220

Pro Asn Gly Ser Cys Trp Gly Ala Gly Glu Glu Asn Cys Gln Arg Leu
225 230 235 240

Thr Lys Ile Ile Cys Ala Gln Gln Cys Ser Gly Arg Cys Arg Gly Lys
245 250 255

Ser Pro Ser Asp Cys Cys His Asn Gln Cys Ala Ala Gly Cys Thr Gly
260 265 270

Pro Arg Glu Ser Asp Cys Leu Val Cys Arg Lys Phe Arg Asp Glu Ala
275 280 285

Thr Cys Lys Asp Thr Cys Pro Pro Leu Met Leu Tyr Asn Pro Thr Thr
290 295 300

Tyr Gln Met Asp Val Asn Pro Glu Gly Lys Tyr Ser Phe Gly Ala Thr
305 310 315 320

Cys Val Lys Lys Cys Pro Arg Asn Tyr Val Val Thr Asp His Gly Ser
325 330 335

Cys Val Arg Ala Cys Gly Ala Asp Ser Tyr Glu Met Glu Glu Asp Gly

-continued

```
            340                 345                 350

Val Arg Lys Cys Lys Lys Cys Glu Gly Pro Cys Arg Lys Val Cys Asn
        355                 360                 365

Gly Ile Gly Ile Gly Glu Phe Lys Asp Ser Leu Ser Ile Asn Ala Thr
    370                 375                 380

Asn Ile Lys His Phe Lys Asn Cys Thr Ser Ile Ser Gly Asp Leu His
385                 390                 395                 400

Ile Leu Pro Val Ala Phe Arg Gly Asp Ser Phe Thr His Thr Pro Pro
                405                 410                 415

Leu Asp Pro Gln Glu Leu Asp Ile Leu Lys Thr Val Lys Glu Ile Thr
            420                 425                 430

Gly Phe Leu Leu Ile Gln Ala Trp Pro Glu Asn Arg Thr Asp Leu His
        435                 440                 445

Ala Phe Glu Asn Leu Glu Ile Ile Arg Gly Arg Thr Lys Gln His Gly
    450                 455                 460

Gln Phe Ser Leu Ala Val Val Ser Leu Asn Ile Thr Ser Leu Gly Leu
465                 470                 475                 480

Arg Ser Leu Lys Glu Ile Ser Asp Gly Asp Val Ile Ile Ser Gly Asn
                485                 490                 495

Lys Asn Leu Cys Tyr Ala Asn Thr Ile Asn Trp Lys Lys Leu Phe Gly
            500                 505                 510

Thr Ser Gly Gln Lys Thr Lys Ile Ile Ser Asn Arg Gly Glu Asn Ser
        515                 520                 525

Cys Lys Ala Thr Gly Gln Val Cys His Ala Leu Cys Ser Pro Glu Gly
    530                 535                 540

Cys Trp Gly Pro Glu Pro Arg Asp Cys Val Ser Cys Arg Asn Val Ser
545                 550                 555                 560

Arg Gly Arg Glu Cys Val Asp Lys Cys Asn Leu Leu Glu Gly Glu Pro
                565                 570                 575

Arg Glu Phe Val Glu Asn Ser Glu Cys Ile Gln Cys His Pro Glu Cys
            580                 585                 590

Leu Pro Gln Ala Met Asn Ile Thr Cys Thr Gly Arg Gly Pro Asp Asn
        595                 600                 605

Cys Ile Gln Cys Ala His Tyr Ile Asp Gly Pro His Cys Val Lys Thr
    610                 615                 620

Cys Pro Ala Gly Val Met Gly Glu Asn Asn Thr Leu Val Trp Lys Tyr
625                 630                 635                 640

Ala Asp Ala Gly His Val Cys His Leu Cys His Pro Asn Cys Thr Tyr
                645                 650                 655

Gly Cys Thr Gly Pro Gly Leu Glu Gly Cys Pro Thr Asn Gly Pro Lys
            660                 665                 670

Ile Pro Ser Ile Ala Thr Gly Met Val Gly Ala Leu Leu Leu Leu Leu
        675                 680                 685

Val Val Ala Leu Gly Ile Gly Leu Phe Met Arg Arg Arg His Ile Val
    690                 695                 700

Arg
705
```

<210> SEQ ID NO 7
<211> LENGTH: 30
<212> TYPE: DNA
<213> ORGANISM: Artificial Sequence
<220> FEATURE:
<223> OTHER INFORMATION: Homo sapiens -continued

<400> SEQUENCE: 7
atataggtac cgccaccatg cgaccctccg 30

<210> SEQ ID NO 8
<211> LENGTH: 33
<212> TYPE: DNA
<213> ORGANISM: Artificial Sequence
<220> FEATURE:
<223> OTHER INFORMATION: Homo sapiens

<400> SEQUENCE: 8
attataagct tagacgagcc ttcctccaga gcc 33

<210> SEQ ID NO 9
<211> LENGTH: 36
<212> TYPE: DNA
<213> ORGANISM: Artificial Sequence
<220> FEATURE:
<223> OTHER INFORMATION: Primer for Haemagglutinin epitope

<400> SEQUENCE: 9
catgaaagct tggctcgtct gggtatccat atgatg 36

<210> SEQ ID NO 10
<211> LENGTH: 24
<212> TYPE: DNA
<213> ORGANISM: Artificial Sequence
<220> FEATURE:
<223> OTHER INFORMATION: Primer for Haemagglutinin epitope

<400> SEQUENCE: 10
ctaatggtag ccggcgcgcc ctcg 24

<210> SEQ ID NO 11
<211> LENGTH: 36
<212> TYPE: DNA
<213> ORGANISM: Artificial Sequence
<220> FEATURE:
<223> OTHER INFORMATION: Homo sapiens

<400> SEQUENCE: 11
atagagctac cggaagcagc gggctggagg aaaaga 36

<210> SEQ ID NO 12
<211> LENGTH: 29
<212> TYPE: DNA
<213> ORGANISM: Artificial Sequence
<220> FEATURE:
<223> OTHER INFORMATION: Homo sapiens

<400> SEQUENCE: 12
cataagcggc cgcttaccga acgatgtgg 29

<210> SEQ ID NO 13
<211> LENGTH: 2220
<212> TYPE: DNA
<213> ORGANISM: Artificial Sequence
<220> FEATURE:
<223> OTHER INFORMATION: Homo sapiens

<400> SEQUENCE: 13
ggtaccgcca ccatgcgacc ctccgggacg gccggggcag cgctcctggc gctgctggct 60
gcgctctgcc cggcgagtcg ggctctggag gaaggctcgt ctaagcttgg ctcgtctggg 120
tatccatatg atgttccaga ttatgctggg gcccagccgg ccagatctgg cggcggcctg 180

-continued

```
aacgacatct tcgaggccca gaagatcgag tggcacgagg gcgcgccggc taccggaagc    240
agcgggctgg aggaaaagaa agtttgccaa ggcacgagta acaagctcac gcagttgggc    300
acttttgaag atcattttct cagcctccag aggatgttca ataactgtga ggtggtcctt    360
gggaatttgg aaattaccta tgtgcagagg aattatgatc tttccttctt aaagaccatc    420
caggaggtgg ctggttatgc cctcattgcc ctcaacacag tggagcgaat tcctttggaa    480
aacctgcaga tcatcagagg aaatatgtac tacgaaaatt cctatgcctt agcagtctta    540
tctaactatg atgcaaataa aaccggactg aaggagctgc ccatgagaaa tttacaggaa    600
atcctgcatg gcgccgtgcg gttcagcaac aaccctgccc tgtgcaacgt ggagagcatc    660
cagtggcggg acatagtcag cagtgacttt ctcagcaaca tgtcgatgga cttccagaac    720
cacctgggca gctgccaaaa gtgtgatcca agctgtccca atgggagctg ctggggtgca    780
ggagaggaga actgccagag actgaccaaa atcatctgtg cccagcagtg ctccgggcgc    840
tgccgtggca agtcccccag tgactgctgc cacaaccagt gtgctgcagg ctgcacaggc    900
ccccgggaga gcgactgcct ggtctgccgc aaattccgag acgaagccac gtgcaaggac    960
acctgccccc cactcatgct ctacaacccc accacgtacc agatggatgt gaaccccgag   1020
ggcaaataca gctttggtgc cacctgcgtg aagaagtgtc cccgtaatta tgtggtgaca   1080
gatcacggct cgtgcgtccg agcctgtggg gccgacagct atgagatgga ggaagacggc   1140
gtccgcaagt gtaagaagtg cgaagggcct tgccgcaaag tgtgtaacgg aataggtatt   1200
ggtgaattta aagactcact ctccataaat gctacgaata ttaaacactt caaaaactgc   1260
acctccatca gtggcgatct ccacatcctg ccggtggcat ttaggggtga ctccttcaca   1320
catactcctc ctctggatcc acaggaactg gatattctga aaaccgtaaa ggaaatcaca   1380
gggtttttgc tgattcaggc ttggcctgaa aacaggacgg acctccatgc ctttgagaac   1440
ctagaaatca tacgcggcag gaccaagcaa catggtcagt tttctcttgc agtcgtcagc   1500
ctgaacataa catccttggg attacgctcc ctcaaggaga taagtgatgg agatgtgata   1560
atttcaggaa acaaaaattt gtgctatgca aatacaataa actggaaaaa actgtttggg   1620
acctccggtc agaaaaccaa aattataagc aacagaggtg aaaacagctg caaggccaca   1680
ggccaggtct gccatgcctt gtgctccccc gagggctgct ggggcccgga gcccagggac   1740
tgcgtctctt gccggaatgt cagccgaggc agggaatgcg tggacaagtg caaccttctg   1800
gagggtgagc caagggagtt tgtggagaac tctgagtgca tacagtgcca cccagagtgc   1860
ctgcctcagg ccatgaacat cacctgcaca ggacggggac cagacaactg tatccagtgt   1920
gcccactaca ttgacggccc ccactgcgtc aagacctgcc cggcaggagt catgggagaa   1980
aacaacaccc tggtctggaa gtacgcagac gccggccatg tgtgccacct gtgccatcca   2040
aactgcacct acggatgcac tgggccaggt cttgaaggct gtccaacgaa tgggcctaag   2100
atcccgtcca tcgccactgg gatggtgggg gccctcctct tgctgctggt ggtggccctg   2160
gggatcggcc tcttcatgcg aaggcgccac atcgttcggt aagcggccgc tcgaggccgg   2220
```

<210> SEQ ID NO 14
<211> LENGTH: 735
<212> TYPE: PRT
<213> ORGANISM: Artificial Sequence
<220> FEATURE:
<223> OTHER INFORMATION: Homo sapiens

<400> SEQUENCE: 14

-continued

```
Gly Thr Ala Thr Met Arg Pro Ser Gly Thr Ala Gly Ala Ala Leu Leu
1               5                   10                  15

Ala Leu Leu Ala Ala Leu Cys Pro Ala Ser Arg Ala Leu Glu Glu Gly
            20                  25                  30

Ser Ser Lys Leu Gly Ser Ser Gly Tyr Pro Tyr Asp Val Pro Asp Tyr
        35                  40                  45

Ala Gly Ala Gln Pro Ala Arg Ser Gly Gly Gly Leu Asn Asp Ile Phe
    50                  55                  60

Glu Ala Gln Lys Ile Glu Trp His Glu Gly Ala Pro Ala Thr Gly Ser
65                  70                  75                  80

Ser Gly Leu Glu Glu Lys Lys Val Cys Gln Gly Thr Ser Asn Lys Leu
                85                  90                  95

Thr Gln Leu Gly Thr Phe Glu Asp His Phe Leu Ser Leu Gln Arg Met
            100                 105                 110

Phe Asn Asn Cys Glu Val Val Leu Gly Asn Leu Glu Ile Thr Tyr Val
        115                 120                 125

Gln Arg Asn Tyr Asp Leu Ser Phe Leu Lys Thr Ile Gln Glu Val Ala
    130                 135                 140

Gly Tyr Ala Leu Ile Ala Leu Asn Thr Val Glu Arg Ile Pro Leu Glu
145                 150                 155                 160

Asn Leu Gln Ile Ile Arg Gly Asn Met Tyr Tyr Glu Asn Ser Tyr Ala
                165                 170                 175

Leu Ala Val Leu Ser Asn Tyr Asp Ala Asn Lys Thr Gly Leu Lys Glu
            180                 185                 190

Leu Pro Met Arg Asn Leu Gln Glu Ile Leu His Gly Ala Val Arg Phe
        195                 200                 205

Ser Asn Asn Pro Ala Leu Cys Asn Val Glu Ser Ile Gln Trp Arg Asp
    210                 215                 220

Ile Val Ser Ser Asp Phe Leu Ser Asn Met Ser Met Asp Phe Gln Asn
225                 230                 235                 240

His Leu Gly Ser Cys Gln Lys Cys Asp Pro Ser Cys Pro Asn Gly Ser
                245                 250                 255

Cys Trp Gly Ala Gly Glu Glu Asn Cys Gln Arg Leu Thr Lys Ile Ile
            260                 265                 270

Cys Ala Gln Gln Cys Ser Gly Arg Cys Arg Gly Lys Ser Pro Ser Asp
        275                 280                 285

Cys Cys His Asn Gln Cys Ala Ala Gly Cys Thr Gly Pro Arg Glu Ser
    290                 295                 300

Asp Cys Leu Val Cys Arg Lys Phe Arg Asp Glu Ala Thr Cys Lys Asp
305                 310                 315                 320

Thr Cys Pro Pro Leu Met Leu Tyr Asn Pro Thr Thr Tyr Gln Met Asp
                325                 330                 335

Val Asn Pro Glu Gly Lys Tyr Ser Phe Gly Ala Thr Cys Val Lys Lys
            340                 345                 350

Cys Pro Arg Asn Tyr Val Val Thr Asp His Gly Ser Cys Val Arg Ala
        355                 360                 365

Cys Gly Ala Asp Ser Tyr Glu Met Glu Glu Asp Gly Val Arg Lys Cys
    370                 375                 380

Lys Lys Cys Glu Gly Pro Cys Arg Lys Val Cys Asn Gly Ile Gly Ile
385                 390                 395                 400

Gly Glu Phe Lys Asp Ser Leu Ser Ile Asn Ala Thr Asn Ile Lys His
                405                 410                 415

Phe Lys Asn Cys Thr Ser Ile Ser Gly Asp Leu His Ile Leu Pro Val
```

-continued

```
            420                 425                 430

Ala Phe Arg Gly Asp Ser Phe Thr His Thr Pro Pro Leu Asp Pro Gln
        435                 440                 445

Glu Leu Asp Ile Leu Lys Thr Val Lys Glu Ile Thr Gly Phe Leu Leu
    450                 455                 460

Ile Gln Ala Trp Pro Glu Asn Arg Thr Asp Leu His Ala Phe Glu Asn
465                 470                 475                 480

Leu Glu Ile Ile Arg Gly Arg Thr Lys Gln His Gly Gln Phe Ser Leu
                485                 490                 495

Ala Val Val Ser Leu Asn Ile Thr Ser Leu Gly Leu Arg Ser Leu Lys
            500                 505                 510

Glu Ile Ser Asp Gly Asp Val Ile Ile Ser Gly Asn Lys Asn Leu Cys
        515                 520                 525

Tyr Ala Asn Thr Ile Asn Trp Lys Lys Leu Phe Gly Thr Ser Gly Gln
    530                 535                 540

Lys Thr Lys Ile Ile Ser Asn Arg Gly Glu Asn Ser Cys Lys Ala Thr
545                 550                 555                 560

Gly Gln Val Cys His Ala Leu Cys Ser Pro Glu Gly Cys Trp Gly Pro
                565                 570                 575

Glu Pro Arg Asp Cys Val Ser Cys Arg Asn Val Ser Arg Gly Arg Glu
            580                 585                 590

Cys Val Asp Lys Cys Asn Leu Leu Glu Gly Glu Pro Arg Glu Phe Val
        595                 600                 605

Glu Asn Ser Glu Cys Ile Gln Cys His Pro Glu Cys Leu Pro Gln Ala
    610                 615                 620

Met Asn Ile Thr Cys Thr Gly Arg Gly Pro Asp Asn Cys Ile Gln Cys
625                 630                 635                 640

Ala His Tyr Ile Asp Gly Pro His Cys Val Lys Thr Cys Pro Ala Gly
                645                 650                 655

Val Met Gly Glu Asn Asn Thr Leu Val Trp Lys Tyr Ala Asp Ala Gly
            660                 665                 670

His Val Cys His Leu Cys His Pro Asn Cys Thr Tyr Gly Cys Thr Gly
        675                 680                 685

Pro Gly Leu Glu Gly Cys Pro Thr Asn Gly Pro Lys Ile Pro Ser Ile
    690                 695                 700

Ala Thr Gly Met Val Gly Ala Leu Leu Leu Leu Leu Val Val Ala Leu
705                 710                 715                 720

Gly Ile Gly Leu Phe Met Arg Arg Arg His Ile Val Arg Ala Ala
                725                 730                 735
```

BIOMOLECULE-RELEASING CELL AND SELECTION THEREOF BY MEANS OF A SURFACE PROTEIN

CROSS REFERENCE TO PRIOR APPLICATIONS

This application is a U.S. National Phase application under 35 U.S.C. § 371 of International Application No. PCT/DE2014/000205, filed on Apr. 20, 2014. The International Application was published in German on Oct. 29, 2015 as WO 2015/161835 A1 under PCT Article 21(2). The International Application is herein incorporated by reference in its entirety.

REFERENCE TO SEQUENCE LISTING SUBMITTED BY EFS-WEB

This application was filed electronically via EFS-Web and includes an electronically submitted sequence listing in .txt format. The .txt file contains a sequence listing entitled “15305162seq_list.txt” created on Oct. 11, 2017, and is 23,463 bytes in size. The sequence listing in this .txt file is part of the specification and is hereby incorporated by reference herein in its entirety.

The present invention relates to a method for selecting cells which release biomolecules, in particular proteins, for example monoclonal antibodies, as well as means that can be used for this.

Attempts have already been made previously to select antibody-producing hybridoma cells, in which the antibodies secreted by the producing cell should be bound at the cell surface thereof, in order to identify the cells, surface-marked in this way, by means of fluorescence-labelled detection antibodies, isolate the identified cells, and then selectively multiply these for the purpose of extracting the antibodies produced by a cell.

EP 1 141 271 B1 discloses a method for selecting monoclonal antibodies which comprises the fusion of B-lymphocytes with myeloma cells to form antibody-producing hybridoma cells, wherein the antibodies are presented on the cell surface of the hybridoma cells by means of an antibody binding protein, as well as the binding of the antibodies to antigens. The antibody binding protein is introduced here into the hybridoma cell via the myeloma cell or via expression vectors. The antibody binding protein has an antibody binding site independent of the specificity of the variable regions of the antibody, and also has a membrane anchor. The produced antibody is exposed at the cell surface via this binding site, such that its specific binding regions can interact with epitopes against which the produced antibody is directed.

In this method according to the prior art, the marking of the cell surfaces is dependent on the affinity of the antibody binding protein to the released antibody. It is thus possible that cells which secrete the desired antibody, which is highly specific to the antigen epitope, in maximum quantity are not identified as being optimal within the scope of the selection, contrary to the objective, since their affinity to the antibody binding protein is lower than that of a sub-optimal antibody less affine to the antigen epitope, wherein the lower affinity of the optimal antibody to the antibody binding protein compared with the sub-optimal antibody potentially cannot be compensated for, not even by greater production quantities of the optimal antibody. This disadvantageous effect is explained by competitive displacement of the potentially optimal antibody by sub-optimal antibodies having greater affinity to the binding protein. In addition, the binding of a secreted antibody to the antibody binding protein can have a negative influence on the expression and secretion of the desired antibody. A further disadvantage is the limitation of the selection method to antibodies on the basis of the antibody binding protein. This method does not cover any other types of synthetic or natural biomolecules.

EP 0 667 896 B1 discloses a method having the same objective as EP 1 141 271 B1, for selecting or analysing cells in accordance with a product secreted and released by the cells. Besides comparable variants, the cell surface is chemically treated here by means of sulfosuccinimidyl-6-(biotinamido) hexanoate, such that the cell surface after this treatment comprises a specifically covalently bonded biotin. As capture component, an antibody conjugated previously with avidin is specifically bonded to this biotin via the avidin component, wherein the binding between avidin and antibody is established via the disulphide bonds of the antibody molecule, which have been reduced to thiol groups, and a reactive maleimide group inserted into the avidin, resulting in the antigen binding sites directed against both isotypes of the light chain of a produced antibody. Similarly to that disclosed in EP 1 141 271 B1, the capture component comprises an antibody or antibody fragments of which the binding sites directed against the product released by the cell are presented at the cell surface. A disadvantage here, however, is the deficient product specificity of the binding sites, which are directed merely against the light chains generally contained in antibody molecules. In addition, it is disadvantageous that this method comprises the mentioned step of chemical biotinylation, which necessitates a separation of the cells to be treated from their growth medium with subsequent resuspension in a solution containing biotinylation reagent. Hybridoma cells used in particular in the case of production of monoclonal antibodies and fused freshly from myeloma cells and B-cells can sustain undesirable damage as a result of this step. Furthermore, the chemical biotinylation requires a cell-specific titration of the amount of biotinylation reagent to be used. Since the reagent causes a specific binding of biotin to surface proteins, it cannot be ruled out that signal cascades conveyed by the modification of the surface proteins will be initiated in the cell metabolism, which lead to the disadvantage of a reduced expression of the desired cell products, which for example can severely reduce the yield of desired monoclonal antibodies.

Both EP 1 141 271 B1 and EP 0 667 896 B1 disclose methods which do not allow reliable identification and selection of the optimal antibody. This is because, according to EP 1 141 271 B1, the affinity of the secreted antibody to the membrane-bound antibody binding protein is independent of the affinity of the secreted antibody to the epitope against which its specific binding sites are directed. The affinity of the antibody to a target epitope, however, is the primary objective of the selection. If the identification precedes a step which cannot be sufficiently controlled or quantified, this has a negative effect on the accuracy of the selection process as a whole. In the case of the method according to EP 0 667 896 B1, the biotinylation step can be controlled and ultimately also quantified, but only together with a cell-specific titration for determining the amount of reagent to be used and a chemical treatment necessitating method steps which significantly impair or eradicate the vitality of the cells and capability thereof to express the protein to be produced. What complicates this further is the fact that the surface-exposed biotin binds an avidin-conjugated capture antibody directed merely against the light chains of the produced antibody, i.e. likewise does not have the affinity (constituting the primary objective of the selection) of the variable antibody regions to a certain epitope of the antigen used for immunisation, but instead has an affinity that at best is isotype-specific in respect of the light chains and does not allow the identification of that antibody, from those produced from a cell mixture, which binds optimally to a target epitope. In order to prevent sub-optimal products which are released by cells that, where possible, are not to be selected from binding to the capture component of the cell releasing the optimal product, a special medium is used in accordance with EP 0 667 896 B1, which is intended to inhibit the diffusion of released products from the immediate environment of the cell producing them on account of low permeability. This approach is disadvantageous since it necessitates a change of the medium, wherein both the change and the low-permeable medium itself can have negative effects on cell vitality, production, and release of the products. A further disadvantage, which lies in the chemical biotinylation, is the possibility of an undesirably high density of biotin exposed on the cell surface, which, on account of the fact that each avidin tetramer has four biotin binding sites, can lead to an undesirable cross-linking of the exposed biotin molecules, which can reduce the survivability in particular of hybridoma cells created freshly by cell fusion.

The object is therefore to overcome the above-mentioned disadvantages of the prior art to the greatest possible extent and to provide means for a reliable and purposeful selection method for biomolecule-releasing cells on the basis of the specific binding properties of the released biomolecules in order to enable an optimised method comprising the binding of the released biomolecules to the surface of the cells producing them.

The object is achieved by a cell characterised by a surface protein having an extracellularly exposed ligation peptide sequence for enzymatic conjugation of an adapter ligand, said adapter ligand being suitable for the indirect or direct coupling of a molecular catcher structure which has at least one specific binding site for the released biomolecules and which is at a distance from the specific binding site, a surface protein characterised by an extracellularly exposable ligation peptide sequence for enzymatic conjugation of an adapter ligand, a nucleic acid characterised by a sequence of bases or base pairs which codes for such surface protein, an expression vector comprising such nucleic acid, optionally the sequence of bases or base pairs is supplemented by further bases or base pairs which code for a signal peptide at the N-terminus of the surface protein, wherein the signal peptide comprises the biological information for initiation of the cellular protein transport in or through biomembranes, and optionally the signal peptide has the signal sequence of the EGF receptor protein, preferably the amino acid sequence MRPSGTAGAALLALLAALCPASRA (SEQ ID NO: 1) from the N- to the C-terminus, a cell receiving such expression vector, and a method for selecting the cells from a multiplicity of cells, comprising an enzymatic conjugation of the adapter ligand with the ligation peptide sequence, the indirect or direct coupling of the molecular catcher structure at a distance from the specific binding site, and the specific binding of at least one of the released biomolecules to the specific binding site, wherein preferred variants will become clear from the respective dependent claims.

The starting point for the invention is a biomolecule, in particular protein-releasing cell, wherein the biomolecule is produced and secreted by the cell, i.e. is generally delivered into the surrounding medium. The secreted biomolecules can be any type of biomolecules which are produced by a cell and, in the case of proteins, are regularly secreted with cleaving of a signal peptide, but also can be secondary substances, such as hormones, antibiotics or alkaloids. The secreted biomolecules can also be protein constructs, antibodies or antibody fragments created for example by means of genetic methods, or can be proteins naturally secreted by cells.

For the sought optimised selection method, the biomolecule-releasing cell is provided with a surface protein which has an extracellularly exposed ligation peptide sequence for enzymatic conjugation of an adapter ligand, said adapter ligand being suitable for the indirect or direct coupling of a molecular catcher structure which has at least one specific binding site for the released biomolecules and which is at a distance from the specific binding site. The ligation peptide sequence should not be confused here with the antibody binder protein known from the prior art. This is because, instead of binding an antibody merely via its Fc part, the ligation peptide sequence serves to bind an adapter ligand which enables docking of practically any molecular catcher structure. Biotin which is conjugated with the ligation peptide sequence in a ratio of 1:1 from full medium in gentle conditions by means of a BirA ligase obtained from *E. coli* is preferably used here. However, the method therefore is not limited to this approach. Other suitable ligation peptide sequences and adapter ligands different from biotin can also be used. It is also possible to dispense with the separate binding of the adapter ligand and the catcher structure and for example to conjugate a construct enzymatically with the ligation peptide sequence which already has the desired properties of the catcher protein and presents a corresponding epitope.

The surface protein is preferably anchored in the cell membrane by means of a membrane-bound component. Alternatively, however, it can also comprise a number of transmembrane domains or can be connected to the cell surface in a different way, for example via interactions with native proteins which, in turn, are already membrane-bound.

Due to the economical significance of monoclonal antibodies, it is advantageous to adapt the method and the means to be provided therefor to hybridoma cells which produce and release monoclonal antibodies. These cells are therefore preferably provided with the surface protein, wherein the catcher structure to be used is an antigen molecular structure and the specific binding site which this antigen molecular structure has is an epitope which is specifically bound via its variable regions by the released antibodies. Cells which release solely antibody fragments can also be used.

In the rarest of cases it is possible to find a native surface protein having the properties necessary for the method in suitable cells. A protein-releasing cell is therefore preferably incited artificially, using methods known from the prior art, to express a surface protein of this type composed from various functional domains, or a precursor which is regularly modified within the scope of the cell metabolism for the desired localisation at the cell surface.

For stable expression of a vector coding for the surface protein or the translocatable and processable precursor thereof, it has proven to be advantageous, prior to the fusion resulting in the hybridoma cell, to transfect the myeloma cell used for this purpose with the genetic information for the surface protein.

In order to be able to use the cells to be provided in the sought optimised selection method, it is necessary for the catcher structure to be exposed at the cell surface via controlled enzymatic conjugation of a separate adapter ligand or an integrated conjugation structure with the surface protein, wherein the catcher structure presents the epitope(s) to be used for the selection. It is generally desirable to separate the enzymatic conjugation with the ligation peptide sequence from the coupling of the molecular catcher structure in order to remain flexible with regard to the choice of the molecular catcher structure. It has proven to be expedient for this purpose to optimise the ligation peptide sequence for enzymatic conjugation with biotin and to covalently bond the molecular catcher structure to a docking molecule, such as one of the biotin ligands avidin, streptavidin or neutravidin, more specifically at a distance from the binding site specific for the released biomolecule.

It is additionally important, for the sought selection method, to provide cells in which the catcher structure is bound, via its specific binding site for the released biomolecule, between such a biomolecule and the surface protein in order to be able to identify the biomolecule thus presented and therefore the cell producing the biomolecule by means of a detection molecule, wherein it is also possible to dispense with a separate detection molecule and for example to directly incorporate an isotope labelling in the biomolecule via the multiplication of the cell in isotope-containing medium.

It is also advantageous for the flexible handling of the sought method when cells are provided in which a separate adapter ligand is bound to the ligation peptide sequence, wherein the binding should preferably be covalent. If a catcher structure is now bonded, usually non-covalently, to an adapted cell of this type, this cell can be used for the sought method. Here, the catcher structure does not necessarily have to be bound to the adapter ligand via an additional docking molecule, but in the case of biotin as adapter ligand it has proven to be expedient to use, for the coupling, a molecular catcher structure covalently bonded to a biotin ligand acting as docking molecule. Since the non-covalent binding of biotin, for example to streptavidin, is one of the strongest known bonds in biological systems, the high affinity between adapter ligand and docking molecule does not have a negative effect on the specificity of the selection method. With use of other adapter ligands and docking molecules, it must be ensured, in the case of non-covalent bonds between these two binding partners, that these have sufficient affinity to one another, and if necessary covalent binding must be avoided, which can be achieved for example by integrating adapter and docking molecules in a molecule.

The surface protein should, as already mentioned, have certain properties in order to enable the sought selection method. What is key here is that the surface protein has an extracellularly exposable ligation peptide sequence, which allows enzymatic conjugation of an adapter ligand, preferably such as biotin, wherein the adapter ligand, as presented above, can also be already integrated into the docking molecule and/or the molecular catcher structure. It has proven to be advantageous when the ligation peptide sequence comprises a biotin acceptor peptide sequence, preferably the amino acid sequence GLNDIFEAQKIEWHE (SEQ ID NO: 2) from the N- to the C-terminus, or matches such a sequence.

It is advantageous when the surface protein is already constructed such that it is anchored in the cell membrane independently of the presence of other membrane proteins. For this purpose it is advantageous when the surface protein has at least one hydrophobic domain for incorporation in a cell membrane. It has proven to be favourable when the ligation peptide sequence of the surface protein, on the basis of its primary structure, is located closer to the N-terminus than the hydrophobic domain. It is particularly favourable for the desired anchoring of the surface protein in the cell membrane if the peptide sequence for the hydrophobic domain has a transmembrane domain of the EGF receptor, wherein EGF stands for "epidermal growth factor". The peptide sequence preferably has the amino acid sequence IATGMVGALLLLLWALGIGLFM (SEQ ID NO: 3) from the N- to the C-terminus for the hydrophobic domain of the surface protein, or matches such a sequence.

Although it is conceivable to arrange the primary structure of the ligation peptide sequence in the direct vicinity of the hydrophobic domain, it is more favourable, for the purpose of extracellularly exposing the ligation peptide sequence of the surface protein, to place the primary structure of an amino acid linker between the ligation peptide sequence and the hydrophobic domain, which linker advantageously comprises the extracellular domain of the mature human EGF receptor, wholly or partially, preferably with the amino acid sequence GAPATGSSGLEEKKVC-
QGTSNKLTQLGTFEDHFLSLQRMFNNCEVVLGNLE-
ITYVQRNYDL SFLKTIQEVAGYALIALNTVERIPLEN-
LQIIRGNMYYENSYALAVLSNYDANKTGLKELPMRNL
QEILHGAVRFSNNPALCNVESIQWRDIVSSDFL-
SNMSMDFQNHLGSCQKCDPSCPNGSCW GAGEENC-
QRLTKIICAQQCSGRCRGKSPSDCCHNQCAAGCTG-
PRESDCLVCRKFRDEATC
KDTCPPLMLYNPTTYQMDVNPEGKYSFGATCVK-
KCPRNYVVTDHGSCVRACGADSYEME EDGVRKCK-
KCEGPCRKVCNGIGIGEFKDSLSINATNIKHFKNCT-
SISGDLHILPVAFRGDSFT
HTPPLDPQELDILKTVKEITGFLLIQAWPENRTDL-
HAFENLEIIRGRTKQHGQFSLAVVSLNIT SLGL-
RSLKEISDGDVIISGNKNLCYANTINWKKLFGTSGQK-
TKIISNRGENSCKATGQVCHAL
CSPEGCWGPEPRDCVSCRNVSRGRECVDKCNL-
LEGEPREFVENSECIQCHPECLPQAMNI TCTGRGP-
DNCIQCAHYIDGPHCVKTCPAGVMGENNTLVWKY-
ADAGHVCHLCHPNCTYGCT GPGLEGCPTNGPKIPS
(SEQ ID NO: 4) from the N- to the C-terminus.

In order to be able to check the presence of the surface protein at the cell surface before carrying out the method, independently of the functional properties of said surface protein desired for the sought optimised selection method, it has proven to be favourable to additionally provide the surface protein with a control epitope, which can be extracellularly exposed, wherein it has proven to be expedient to place the primary structure of this control epitope closer to the N-terminus than the ligation peptide sequence. The peptide sequence for the control epitope preferably forms haemagglutinin-A epitope, preferably with the amino acid sequence YPYDVPDYA (SEQ ID NO: 5) from the N- to the C-terminus. After specific interaction with an antibody directed against this control epitope and labelling thereof, it is possible to assess, for example by means of cytometry or fluorescence microscopy, whether the surface protein is present at the cell membrane.

In order to overcome the disadvantage of the prior art, in which it cannot be ruled out that interactions of antibodies or reagents with the cell surface will trigger metabolic cascades and feedback effects in the cell metabolism, which have a negative effect on the vitality of the cell and/or the capability thereof to multiply, produce and/or release desired biomolecules, and also to produce and/or localise the surface protein, it is therefore significant for the optimisation of the sought method that the interaction of the ligation peptide taking place during and after the enzymatic conjugation of the ligation peptide does not trigger any of the mentioned negative effects. A surface protein having an overall structure which is free from actin-, DNA-, or RNA-binding motifs, from nucleus-localising signals, from Golgi or ER retention signals, from signals for transport from the cell membrane to the Golgi, and, in terms of the primary structure at least between the hydrophobic domain and C-terminus, free from phosphorylatable tyrosine residues is therefore particularly reliable, preferably having the amino acid sequence LEEGSSKLGSSGYPYDVPDYAGAQ-PARSGGGLNDIFEAQKIEWHEGAPATGSSGLEEKKV CQGTSNKLTQLGTFEDHFLSLQRMFNNCEVVLGN-LEITYVQRNYDLSFLKTIQEVAGYALIAL NTVERIPLENLQIIRGNMYYENSYALAVLSNYDANK-TGLKELPMRNLQEILHGAVRFSNNPAL CNVESIQWR-DIVSSDFLSNMSMDFQNHLGSCQKCDPSCPNGSCW-GAGEENCQRLTKIICA QQCSGRCRGKSPSDCCHNQCAAGCTGPRESD-CLVCRKFRDEATCKDTCPPLMLYNPTTY QMDVN-PEGKYSFGATCVKKCPRNYVVTDHGSCVRAC-GADSYEMEEDGVRKCKKCEGPC RKVCNGIGIGEFKDSLSINATNIKHFKNCTSISGDL-HILPVAFRGDSFTHTPPLDPQELDILKTV KEITG-FLLIQAWPENRTDLHAFENLEIIRGRTKQHGQFSLAV-VSLNITSLGLRSLKEISDGDVII SGNKNLCYANTINWKKLFGTSGQKTKIISNRGEN-SCKATGQVCHALCSPEGCWGPEPRDC VSCRNVSR-GRECVDKCNLLEGEPREFVENSECIQCHPECLPQAM-NITCTGRGPDNCIQCA HYIDGPHCVKTCPAGVMGENNTLVWKY-ADAGHVCHLCHPNCTYGCTGPGLEGCPTNGPKI PSI-ATGMVGALLLLLVVALGIGLFMRRRHIVR (SEQ ID NO: 6) from the N- to the C-terminus.

So that the surface protein can overcome the cell membrane at least in part and can present the desired structures at the cell surface, it is generally necessary for it to be cytoplasmically translated as a precursor, which is characterised by a signal peptide, wherein the signal peptide is regularly cleaved off, i.e. processed, during the course of the translocation. A means to be provided generally for the sought optimised selection method is therefore a nucleic acid having a sequence of bases or base pairs which codes for the surface protein with a signal peptide at the N-terminus, wherein the signal peptide has the biological information for initiation of the cellular protein transport in or through biomembranes. It has proven to be advantageous when the signal peptide has the signal sequence of the EGF receptor protein, preferably the amino acid sequence MRPS-GTAGAALLALLAALCPASRA (SEQ ID NO: 1) from the N- to the C-terminus.

The nucleic acid is expediently provided in such a way that the nucleic acid is integrated into an expression vector either uninterrupted or interrupted by further bases or base pairs, wherein a person skilled in the art additionally knows to choose promoters conducive to effective expression.

The expression vector is in turn introduced into a cell for the sought optimised selection method. If hybridoma cells which produce monoclonal antibodies are to be subjected to the sought method, it is advantageous to introduce the expression vector into the myeloma cells prior to the fusion of B-cells and myeloma cells to form hybridoma cells, and to allow the fusion to occur subsequently.

So as to be able to work from the outset with cells which could be successfully transfected with the expression vector for the nucleic acid of the surface protein or precursor thereof, it is advantageous when the expression vector comprises a resistance gene against an antibiotic or a cell toxin, wherein resistance genes coding for resistances against amino glycoside antibiotics, such as gentamicins, have proven to be advantageous, as have resistance genes coding for resistances against the cell toxin puromycin or salts thereof. The cells can thus be cultured from the outset using a growth medium which comprises the corresponding antibiotic or cell toxin, and said cells are resistant to the antibiotic or the cell toxin and consequently were successfully transfected with the expression vector and have the surface protein at their surface.

Using the cells that contain the expression vector and carry the surface protein at the cell surface, it is possible to carry out the optimised method for selection of cells that release biomolecules. The method makes it possible to select, from a multiplicity of cells, those which comprise the biomolecule having the best affinity to a certain target molecule and which produce and release this most efficiently. Such a method comprises an enzymatic conjugation of the adapter ligand with the ligation peptide sequence, the indirect or direct coupling of the molecular catcher structure at a distance from the specific binding site, and the specific binding of at least one of the released biomolecules at the binding site.

The method advantageously also includes the labelling of the biomolecule bound to the catcher structure by means of a detection antibody bound to a carrier and directed against the biomolecule, a detection antibody fragment, or another molecular detection structure binding with high affinity to the biomolecule. The carrier and detection structure can also be integrated in a molecule.

In a preferred variant of the method, the carrier or the molecular detection structure emits electromagnetic waves and/or is magnetic or magnetisable and/or is immobilised. It is thus possible to use detection methods known to a person skilled in the art, for example flow through cytometry, fluorescence microscopy, or also affinity chromatography.

A particular advantage of the method lies in the fact that, when the released biomolecule is an antibody or antibody fragment and the detection structure, the detection antibody, or the detection antibody fragment is directed against the isotype-specific or subclass-specific region of the released antibody, it is possible to determine the isotype and/or the subclass of the released product. This is therefore advantageous because a specific cell, selected as optimal, can thus be transferred directly into a cell culture, and at the same time there is already clarity with regard to the subclass of the produced antibody or antibody fragment. Certain subclasses, which in accordance with the prior art can be determined only after stabilisation of the hybridoma and corresponding purification of the antibody or antibody fragment, are preferred for many applications.

To summarise, the method presented here is based on the fact that a specific coupling of a binding site specific for the biomolecule released by the cell to a catcher structure is successful, which makes it possible to bind the released biomolecule specifically at the cell surface and then to detect said biomolecule, wherein the advantages of a universally usable adapter system can additionally be used, such that the method is not limited to antibody-producing cells, but instead any cell can be selected which produces and releases a biomolecule of interest, based on the affinity of the biomolecule to a desired target structure and the produced and released quantity of the biomolecule. Here, the difference from the prior art lies in particular in the fact that the catcher structure is already provided at the cell surface in a specific manner, and the binding of the biomolecule to the catcher structure is also specific because it is based on the most unique recognition structure possible for the sought biomolecule. Based on the selection of monoclonal antibodies in accordance with the new method, it is important that, on the one hand, the catcher structure is presented at the cell surface in a controlled manner and the monoclonal antibody released by the cell is bound to the molecular catcher structure via its variable, epitope-specific binding region, and, on the other hand, a binding of the released monoclonal antibody via its non-molecule-individual Fc part is avoided, which from the outset would reduce the specificity of the selection without the possibility to remedy this deficiency by subsequent specific binding to detection structures. The possibility of gentle cell treatment, which makes it possible to directly transfer cytometrically separated cells into the cell culture, is also significant for the success of the new method. Due to a metabolically neutral surface protein in the conjugated and unconjugated state, a method-independent cell multiplication, production and release are ensured. Lastly, the method can be used for a wide range of different biomolecules on account of the used adapter technique, and therefore is not limited to antibodies.

The method according to the invention and the means to be provided therefor will be explained on the basis of the drawings and an exemplary embodiment, in which the expression vector illustrated in FIG. 2 for the surface protein illustrated in FIG. 4 as primary structure is introduced into myeloma cells, which hereinafter will be fused with B-lymphocytes (B-cells for short) to form antibody-producing hybridoma cells.

KEY

1 hybridoma cell
2 enzymatically biotinylated synthetic surface protein
3 expression vector
4 monoclonal antibody
5 streptavidin
6 streptavidin-bound antigen
7 detection antibody
8 detection antibody-bound fluorescence labelling
9 signal sequence
10 haemagglutinin-A epitope sequence and biotin acceptor peptide sequence
11 sequence for the N-terminal part of the mature EGF receptor
12 myeloma cell
13 haemagglutinin-A epitope
14 haemagglutinin-A antibody
15 fluorescence-labelled marker antibody
16 interface
17 signal sequence
18 linker
19 haemagglutinin-A epitope
20 linker
21 biotin acceptor peptide
22 linker
23 extracellular domain of the EGF receptor
24 transmembrane domain of the EGF receptor
25 translation stop interface
26 surface protein including signal sequence

BRIEF DESCRIPTION OF THE DRAWINGS

FIG. 4 shows the protein sequence (26) of the 5'3' Frame for the surface protein including the cleavable amino-terminal signal sequence, wherein the individual protein regions are separated from one another and numbered, although a continuous polypeptide chain is illustrated. An interface (16) can be seen at the N-terminus, followed by the signal sequence (17), followed by a first linker (18), followed by the haemagglutinin-A epitope (19), followed by a second linker (20), followed by the biotin acceptor peptide (21), followed by a third linker (22), followed by the extracellular domain of the EGF receptor (23), followed by the transmembrane domain of the EGF receptor (24) and lastly a translation stop interface.

STRUCTURE OF THE EXPRESSION VECTOR

Figure 1:
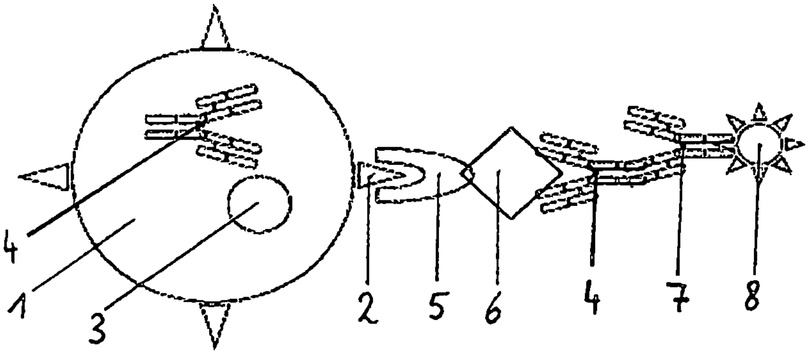
FIG. 1 shows the principle forming the basis of the method according to the invention. Here, the hybridoma cell (1) producing the monoclonal antibody (4) comprises the expression vector (3), which expresses a synthetic surface protein including signal sequence (FIG. 4, reference 26) and presents this, after translocation, in processed form at the cell surface, which surface protein is shown here in enzymatically biotinylated form (2) and is coupled to streptavidin (5) conjugated with the antigen (6) against which the secreted monoclonal antibody (4) is directed, wherein the secreted monoclonal antibody (4) can be detected via a detection antibody-bound fluorescence labelling (9), which is bound to the secreted monoclonal antibody (4) via the detection antibody (8), and, together with said monoclonal antibody (4), the hybridoma cell (1) releasing said antibody (4) can also be detected.
Figure 2:
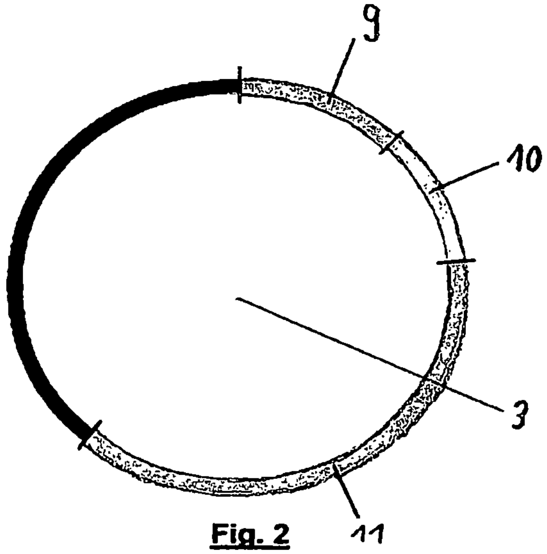
FIG. 2 shows a schematic illustration of the structure of the insert for the expression vector (3) for the surface protein (FIG. 4, reference 26) with the signal sequence (9), the haemagglutinin-A epitope sequence and biotin acceptor sequence (10), and the sequence for the N-terminal part of the EGF receptor (11).
Figure 3:
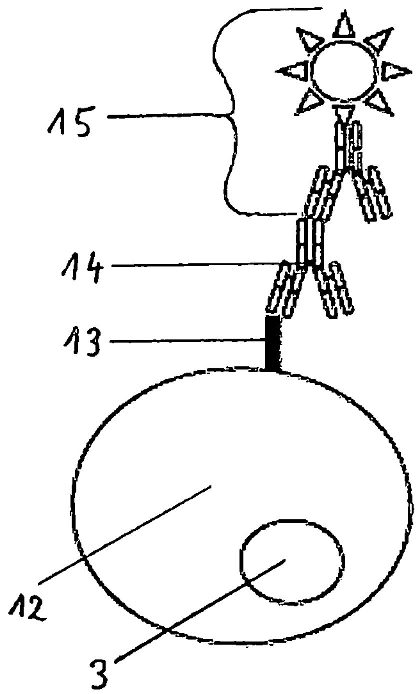
FIG. 3 shows a schematic illustration of the test for successfully transfected myeloma cells (12), which comprise the expression vector (3), by means of the haemagglutinin-A epitope (13), which is presented in an integrated manner at the surface protein exposed at the cell surface and binds to a haemagglutinin-A antibody (14), which in turn binds to a fluorescence-labelled marker antibody (15), thus enabling detection.

To construct the expression vector, the DNA sequences are cloned in the following order from the N- to the C-terminus:

Signal peptide of the unmature human EGF receptor:

```
forward primer
                                    (SEQ ID NO: 7)
5' ATATAGGTACCGCCACCATGCGACCCTCCG 3'

backward primer
                                    (SEQ ID NO: 8)
5' ATTATAAGCTTAGACGAGCCTTCCTCCAGAGCC 3'
```

Haemagglutinin epitope with biotin acceptor peptide:

forward primer (SEQ ID NO: 9)

5' CATGAAAGCTTGGCTCGTCTGGGTATCCATATGATG 3' backward primer (SEQ ID NO: 10)

5' CTAATGGTAGCCGGCGCGCCCTCG 3'

Extracellular domain and transmembrane domain of the mature human EGF receptor:

forward primer (SEQ ID NO: 11)

5' ATAGAGCTACCGGAAGCAGCGGGCTGGAGGAAAAGA 3' backward primer (SEQ ID NO: 12)

5' CATAAGCGGCCGCTTACCGAACGATGTGG3'

Structure of the plasmid pCEP4 with the sequence for the surface protein including the signal sequence; interfaces are underlined; the Kozak sequence is in bold followed by the start ATG for the signal sequence:

(SEQ ID NO: 13)

GGTACCGCCACCATGCGACCCTCCGGGACGGCCGGGGCAGCGCTCCTGGCGCTGCT

GGCTGCGCTCTGCCCGGCGAGTCGGGCTCTGGAGGAAGGCTCGTCTAAGCTTGGCTC

GTCTGGGTATCCATATGATGTTCCAGATTATGCTGGGGCCCAGCCGGCCAGATCTGGC

GGCGGCCTGAACGACATCTTCGAGGCCCAGAAGATCGAGTGGCACGAGGGCGCGCCG

GCTACCGGaAGCAGCGGGCTGGAGGAAAAGAAAGTTTGCCAAGGCACGAGTAACAAGC

TCACGCAGTTGGGCacTTTTGAAGATCATTTTCTCAGCCTCCAGAGGATGTTCAATAACT

GTGAGGTGGTCCTTGGGAATTTGGAAATTACCTATGTGCAGAGGAATTATGATCTTTCCT

TCTTAAAGACCATCCAGGAGGTGGCTGGTTATGCCCTCATTGCCCTCAACACAGTGGAG

CGAATTCCTTTGGAAAACCTGCAGATCATCAGAGGAAATATGTACTACGAAAATTCCTAT

GCCTTAGCAGTCTTATCTAACTATGATGCAAATAAAACCGGACTGAAGGAGCTGCCCAT

GAGAAATTTACAGGAAATCCTGCATGGCGCCGTGCGGTTCAGCAACAACCCTGCCCTG

TGCAACGTGGAGAGCATCCAGTGGCGGGACATAGTCAGCAGTGACTTTCTCAGCAACA

TGTCGATGGACTTCCAGAACCACCTGGGCAGCTGCCAAAAGTGTGATCCAAGCTGTCC

CAATGGGAGCTGCTGGGGTGCAGGAGAGGAGAACTGCCAGAGACTGACCAAAATCATC

TGTGCCCAGCAGTGCTCCGGGCGCTGCCGTGGCAAGTCCCCCAGTGACTGCTGCCAC

AACCAGTGTGCTGCAGGCTGCACAGGCCCCCGGGAGAGCGACTGCCTGGTCTGCCGC

AAATTCCGAGACGAAGCCACGTGCAAGGACACCTGCCCCCCACTCATGCTCTACAACC

CCACCACGTACCAGATGGATGTGAACCCCGAGGCCAAATACAGCTTTGGTGCCACCTG

CGTGAAGAAGTGTCCCCGTAATTATGTGGTGACAGATCACGGCTCGTGCGTCCGAGCC

TGTGGGGCCGACAGCTATGAGATGGAGGAAGACGGCGTCCGCAAGTGTAAGAAGTGC

GAAGGGCCTTGCCGCAAAGTGTGTAACGGAATAGGTATTGGTGAATTTAAAGACTCACT

CTCCATAAATGCTACGAATATTAAACACTTCAAAAACTGCACCTCCATCAGTGGCGATCT

CCACATCCTGCCGGTGGCATTTAGGGGTGACTCCTTCACACATACTCCTCCTCTGGATC

CACAGGAACTGGATATTCTGAAAACCGTAAAGGAAATCACAGGGTTTTTGCTGATTCAG

GCTTGGCCTGAAAACAGGACGGACCTCCATGCCTTTGAGAACCTAGAAATCATACGCG

GCAGGACCAAGCAACATGGTCAGTTTTCTCTTGCAGTCGTCAGCCTGAACATAACATCC

TTGGGATTACGCTCCCTCAAGGAGATAAGTGATGGAGATGTGATAATTTCAGGAAACAA

AAATTTGTGCTATGCAAATACAATAAACTGGAAAAAACTGTTTGGGACCTCCGGTCAGAA

AACCAAAATTATAAGCAACAGAGGTGAAAACAGCTGCAAGGCCACAGGCCAGGTCTGC

CATGCCTTGTGCTCCCCCGAGGGCTGCTGGGGCCCGGAGCCCAGGGACTGCGTCTCT

TGCCGGAATGTCAGCCGAGGCAGGGAATGCGTGGACAAGTGCAACCTTCTGGAGGGT

GAGCCAAGGGAGTTTGTGGAGAACTCTGAGTGCATACAGTGCCACCCAGAGTGCCTGC

CTCAGGCCATGAACATCACCTGCACAGGACGGGGACCAGACAACTGTATCCAGTGTGC

-continued

```
CCACTACATTGACGGCCCCCACTGCGTCAAGACCTGCCCGGCAGGAGTCATGGGAGAA

AACAACACCCTGGTCTGGAAGTACGCAGACGCCGGCCATGTGTGCCACCTGTGCCATC

CAAACTGCACCTACGGATGCACTGGGCCAGGTCTTGAAGGCTGTCCAACGAATGGGCC

TAAGATCCCGTCCATCGCCACTGGGATGGTGGGGGCCCTCCTCTTGCTGCTGGTGGTG

GCCCTGGGGATCGGCCTCTTCATGCGAAGGCGCCACATCGTTCGGTAAGCGGCCGCT

CGAGGCCGG
```

The cloning is performed via standard PCR techniques. The composed construct is also cloned via PCR into the pPB EF1alpha vector so as to enable transfection by means of the PiggyBac transposase system.

The protein sequence of the 5'3' Frame is

```
                                          (SEQ ID NO: 14)
GTATMRPSGTAGAALLALLAALCPASRALEEGSSKLGSSGYPYDVPDYAG

AQPARSGGGLNDIFEAQKIEWHEGAPATGSSGLEEKKVCQGTSNKLTQLG

TFEDHFLSLQRMFNNCEVVLGNLEITYVQRNYDLSFLKTIQEVAGYALIA

LNTVERIPLENLQIIRGNMYYENSYALAVLSNYDANKTGLKELPMRNLQE

ILHGAVRFSNNPALCNVESIQWRDIVSSDFLSNMSMDFQNHLGSCQKCDP

SCPNGSCWGAGEENCQRLTKIICAQQCSGRCRGKSPSDCCHNQCAAGCTG

PRESDCLVCRKFRDEATCKDTCPPLMLYNPTTYQMDVNPEGKYSFGATCV

KKCPRNYVVTDHGSCVRACGADSYEMEEDGVRKCKKCEGPCRKVCNGIGI

GEFKDSLSINATNIKHFKNCTSISGDLHILPVAFRGDSFTHTPPLDPQEL

DILKTVKEITGFLLIQAWPENRTDLHAFENLEIIRGRTKQHGQFSLAVVS

LNITSLGLRSLKEISDGDVIISGNKNLCYANTINWKKLFGTSGQKTKIIS

NRGENSCKATGQVCHALCSPEGCWGPEPRDCVSCRNVSRGRECVDKCNLL

EGEPREFVENSECIQCHPECLPQAMNITCTGRGPDNCIQCAHYIDGPHCV

KTCPAGVMGENNTLVWKYADAGHVCHLCHPNCTYGCTGPGLEGCPTNGPK

IPSIATGMVGALLLLLVVALGIGLFMRRRHIVR-AA
```

and starts with an interface (amino acids 1 to 4), followed by the signal sequence (amino acids 5 to 28), followed by a linker (amino acids 29 to 40), followed by the haemagglutinin-A epitope (amino acids 41 to 49), followed by a linker (amino acids 50 to 58), followed by the biotinylation sequence (amino acids 59 to 73), followed by a linker (amino acids 74 to 82), followed by the extracellular domain of the EGF receptor protein (amino acids 83 to 703), followed by the hydrophobic transmembrane domain of the EGF receptor protein (amino acids 704 to 726), followed by a translation stop and an interface (amino acids 727 to 735).

Monitoring of the Successful Expression and Surface Presentation of the Surface Protein Via the Haemagglutinin Epitope $3\times10^5$ successfully transfected myeloma cells are checked by means of immunofluorescence for the expression and surface presentation of the surface protein. For this purpose, the myeloma cells are plated on glass slides coated with poly-L-lysine and drawn into cell culture medium, that is to say 2 mL DMEM mixed with 3 μg puromycin, at 37° C. and 8% $CO_2$. The myeloma cells are then washed with sterile phosphate-buffered saline solution (hereinafter: PBS) and fixed with 4% paraformaldehyde for 20 min. After the fixing, a washing step with PBS is performed. The glass slides are then incubated for 20 min at room temperature in a block solution, that is to say 1% bovine serum albumin in PBS, then washed and dyed using a mouse anti-haemagglutinin antibody, 1 μg on $1\times10^6$ cells, and a phycoerythrin-labelled $F(ab)_2$ fragment of a donkey-anti-mouse antibody, 0.5 μg/mL in block solution, containing 1×PBS mixed with 5% neonatal calf serum. The glass slides are then washed twice with PBS and twice with distilled water and preserved using an embedding medium. The dyeing is analysed by means of a fluorescence microscope.

Obtaining an Antibody-Producing B-Cell Intended for the Fusion

In order to induce antigen-specific B-lymphocytes in a mouse, the mice are immunised with the antigen of choice. A suitable immunisation procedure depending on the type of antigen is devised for this purpose. For antigens over 25 kDA, this is carried out as standard without further coupling procedures. Antigens below this size are coupled for an adequate immune response to a larger carrier protein, such as bovine serum albumin, ovalbumin, or limpet haemocyanin. The first immunisation preferably includes 100 μg antigen and is administered intraperitoneally together with an adjuvant. After 4-8 weeks a second immunisation is performed without adjuvant, and a blood sample is taken 7 days later. The produced serum is tested by means of a standard immunoassay for the antibodies against the immunised antigen, as explained in greater detail below in section titled "Coupling of the molecular catcher structure at a distance from the epitope to streptavidin". Following a positive response of the mouse, spleen cells thereof are isolated and counted. In parallel, cells of the cell line provided for the fusion are also prepared and used in appropriate quantity for the fusion.

Fusion to Form a Hybridoma Cell

Spleen cells and myeloma cells are preferably used in a ratio of 3:1 for fusion. For this purpose, the cells are placed in fusion buffer, specifically 125 mM NaCl, 5 mM KCL, 4 mM $CaCl_2$, 2.5 mM $MgCl_2$ and 5 mM Tris-HCl pH=7.4, and taken up in the fusion buffer. The cells fuse via electroporation at a DC voltage of 500-700 V and a pulse duration of 20 μs. The cell pellet is resuspended in 200 μL fusion buffer and mixed with 200 μL PEG8000 solution. The cell solution is then transferred into an electroporation cuvette with an electrode spacing of 0.2 cm, and the electroporation is carried out. The cells are then incubated for a further 3 min in the cuvette and are then transferred into selection medium, for example DMEM mixed with 20% foetal calf serum, 2 mM glutamine, 50 μM beta-mercaptoethanol, 200 μM hypoxanthine, 12 μM azaserine, 32 μM 2"-deoxythymidine and 5 μg/mL puromycin, and cultivated until they are sorted.

Enzymatic Biotinylation of the Ligation Peptide Sequence

The enzymatic biotinylation via the transgenically conveyed acceptor peptide is carried out by addition of 1 mM ATP, 10 μM biotin and 0.79 μg per $1\times10^6$ BirA cells for 30 min at room temperature. The cells can then be loaded with the antigen-streptavidin conjugate.

Coupling of the Molecular Catcher Structure at a Distance from the Epitope to Streptavidin Antigens are coupled to streptavidin, for globular proteins, via the homobifunctional cross-linker glutaraldehyde. For ovalbumin, 3 mg protein are mixed with 2 mg streptavidin and 0.25% glutaraldehyde in 1 mL 1×PBS (PBS stands for phosphate-buffered saline solution), and incubated for 2 h at 4° C. The reaction batch is then dialysed for 1 h against 5 L 1×PBS. It is advantageous to check the coupling of proteins to streptavidin with the aid of an enzyme immunoassay. For the enzyme immunoassay, 10 μg of a bovine serum albumin-biotin conjugate are diluted in 1 mL 1×PBS and used to coat the microtitre plate. The coating is performed overnight at 4° C. in a humidity chamber. After the washing of the bowls with mains water, these are then saturated with a block solution, containing 1×PBS mixed with 5% neonatal calf serum (hereinafter: NKS), for 1 h at room temperature (hereinafter: RT). A washing step is then carried out again, as well as the addition of the coupling conjugate in a concentration of 10 μg/mL diluted in the block solution for 1 h at RT. Following another washing step, the coupled antigen is bound by means of a murine monoclonal anti-ovalbumin antibody, 1 μg/mL diluted in block solution. The incubation is also carried out for 1 h at RT. The detection of the anti-ovalbumin antibody is carried out after the washing step by means of a peroxidase-conjugated goat-anti-mouse antibody in a dilution of 1:5000 in block solution for 45 min at RT. Further washing steps are then carried out as well as the addition of a substrate solution, specifically 0.1 M $Na_2H_2PO_4$, 0.1% urea/$H_2O_2$, 1.2 mg/mL tetramethylbenzidine diluted in ethanol, in a ratio of 5:4:1. The substrate reaction is then stopped with 1 M $H_2SO_4$ and measured in an ELISA reader at a wavelength of 450 nm.

Coupling of the Catcher Structure-Streptavidin Conjugate to the Producing Cell Via the Biotinylated Surface Protein For the coupling of the catcher structure-streptavidin conjugate, the producing cells are biotinylated in vitro beforehand for 30 min according to the above section titled "Enzymatic biotinylation of the ligation peptide sequence". $1\times10^6$ cells are then loaded for 20 min by addition of 33 μg of the antigen-streptavidin conjugate. The cells are then centrifuged and taken up in fresh cell culture medium. A 3-4 hour incubation was performed at 37° C. and 8% $CO_2$ in order to start the antibody production of the cells.

Coupling of the Detection Antibody to the Caught Antibody

The cells are transferred into a reaction vessel and pelletised with a 1% bovine serum albumin solution, mixed with 2 mM ethylenediaminetetraacetic acid, at 200×g for 8 min. The cell pellet is resuspended again in block solution according to the above section titled "Coupling of the molecular catcher structure at a distance from the epitope to streptavidin" and incubated on ice with fluorescein isothiocyanate-labelled goat-anti-mouse antibody in a concentration of preferably 1 μg per $1\times10^6$ cells.

Identification of the Optimal Cells by Flow Through Cytometry

A new washing step is then performed, and the cell pellet is taken up in 300 μL buffer for a fluorescence-activated cell sorter, specifically 0.5% bovine serum albumin, 0.01% $NaN_3$ in PBS. The positively labelled cells, which produce the desired antibody which has bonded its antigen in a specific manner on the cell, are then sorted out by the sorting function of the flow through cytometer. The obtained fraction is pelletised by centrifugation.

Transfer of the Optimal Cells into the Cell Culture

The cell pellet is then taken up in full medium, for example RPMI 1640, 10% foetal calf serum, 2 mM glutamine, 50 μM beta-mercaptoethanol, and transferred to 96-well cell culture plates. The cell culture plates already contain a feeder cell population, which has been isolated from mouse peritoneum and which assists the growth of the freshly fused and sorted hybridoma cells.

The invention claimed is:

1. A biomolecule-releasing cell comprising a surface protein having an extracellularly exposed ligation peptide sequence comprising a biotin acceptor peptide sequence comprising the amino acid sequence of SEQ ID NO: 2 for enzymatic conjugation of an adapter ligand that is suitable for indirect or direct coupling of a molecular catcher structure having at least one specific binding site for a released biomolecule from the biomolecule-releasing cell which is at a distance from the specific binding site.

2. The biomolecule-releasing cell according to claim 1, wherein the molecular catcher structure is an antigenic molecular structure, the specific binding site is an epitope of the antigenic molecular structure, and the released biomolecule is an antibody or antibody constituent directed against the epitope.

3. The biomolecule-releasing cell according to claim 1, wherein the molecular catcher structure is bound via its specific binding site between one of the released biomolecules and the surface protein.

4. A method for selecting biomolecule-releasing cells according to claim 1 from a multiplicity of cells, comprising conjugating enzymatically an adapter ligand with the extracellularly exposed ligation peptide sequence of the surface protein on the biomolecule-releasing cell, indirectly or directly coupling a molecular catcher structure comprising at least one specific binding site for a biomolecule released from the biomolecule-releasing cell, and detecting specific binding of the released biomolecule to the specific binding site of the molecular catcher structure.

5. The method according to claim 4, wherein the molecular catcher structure is bound to a docking molecule selected from any one of an avidin, a streptavidin and a neutravidin, and wherein the docking molecule is bound to the adapter ligand.

6. The method according to claim 4, wherein the detecting of specific binding of the released biomolecule to the specific binding site is performed with a detection antibody bound to a carrier and directed against the biomolecule released from the biomolecule-releasing cell, a detection antibody fragment, or another agent that binds with high affinity to the biomolecule released from the biomolecule-releasing cell.

7. The method according to claim 6, wherein the carrier or the agent emits electromagnetic waves and/or is magnetic or magnetisable and/or is immobilised.

8. The method according to claim 6, wherein the released biomolecule is an antibody, and wherein the detection antibody or the detection antibody fragment is directed against an isotype- or a subclass-specific region of the released biomolecule.

9. The method according to claim 4, further comprising sorting the biomolecule-releasing cells from the multiplicity of cells by flow through cytometry.

* * * * *